(12) United States Patent
Carter

(10) Patent No.: US 11,589,744 B2
(45) Date of Patent: Feb. 28, 2023

(54) OPHTHALMIC FIXATION APPARATUS AND METHOD OF USE

(71) Applicant: Troy Lee Carter, Abilene, TX (US)

(72) Inventor: Troy Lee Carter, Abilene, TX (US)

( * ) Notice: Subject to any disclaimer, the term of this patent is extended or adjusted under 35 U.S.C. 154(b) by 0 days.

(21) Appl. No.: 17/029,810

(22) Filed: Sep. 23, 2020

(65) Prior Publication Data

US 2022/0265138 A1    Aug. 25, 2022

(51) Int. Cl.
*A61B 3/00*  (2006.01)
*A61B 3/135*  (2006.01)

(52) U.S. Cl.
CPC .......... *A61B 3/0091* (2013.01); *A61B 3/0008* (2013.01); *A61B 3/135* (2013.01)

(58) Field of Classification Search
CPC ..... A61B 3/0091; A61B 3/0008; A61B 3/135; A61B 3/0083
USPC ......................................................... 351/211
See application file for complete search history.

(56) References Cited

U.S. PATENT DOCUMENTS

| | | | | |
|---|---|---|---|---|
| 5,523,808 A | * | 6/1996 | Kohayakawa | A61B 3/18 600/401 |
| 9,854,965 B2 | * | 1/2018 | Durr | A61B 3/0025 |
| 2021/0153735 A1 | * | 5/2021 | Tsukada | A61B 3/145 |
| 2021/0393122 A1 | * | 12/2021 | Milea | A61B 3/12 |
| 2022/0125307 A1 | * | 4/2022 | Nitta | A61B 3/1208 |

* cited by examiner

*Primary Examiner* — Mohammed A Hasan
(74) *Attorney, Agent, or Firm* — Leavitt Eldredge Law Firm

(57) ABSTRACT

A ophthalmic fixation apparatus includes a case housing with an interior area to hold a power source, the case housing further having a switch to activate a first fixation element and a second fixation element; one or more straps extending from the case housing; a first flexible conduit extending from the case housing and to facilitate direction of the first fixation element; and a second flexible conduit extending from the case housing and to facilitate direction of the second fixation element; the ophthalmic apparatus is for use during an eye exam to keep the patient's attention and maintain a still eye for examination.

18 Claims, 3 Drawing Sheets

OPHTHALMIC FIXATION APPARATUS AND METHOD OF USE

BACKGROUND

1. Field of the Invention

The present invention relates generally to lighting devices and systems for eye exams, and more specifically, to an ophthalmic fixation apparatus that can be easily secured to a slit lamp and provides for two flexible conduits that allow for easy positioning of fixation targets for user convenience. Further, the apparatus includes a toggle switch and a light indicator that makes switching between the two fixation targets easy and effective.

2. Description of Related Art

During a conventional eye exam, a physician may utilize a slit lamp or similar device to examine a patient's eyes. Slit lamps utilize lighting systems, wherein a light is used by the physician to take a closer look at the different structures of the eyes. Conventional systems do not include adequate movement and use of a fixation element, thereby limiting the physician's ability to direct the patient to focus on a particular location. Such a limitation hinders the physicians ability to adequately conduct an examination.

Accordingly, it would be desirable, and is an object of the present invention, to provide a fixation apparatus that includes one or more flexible conduits that allow for vast adjustment of the fixation targets direction by the slit lamp operator. Further, in some embodiments the apparatus includes easy switching between a first target and a second or more targets. Yet further, the apparatus provides for a visual indicator to the physician of which target is active.

Accordingly, although great strides have been made in the area of lighting devices for eye exams, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
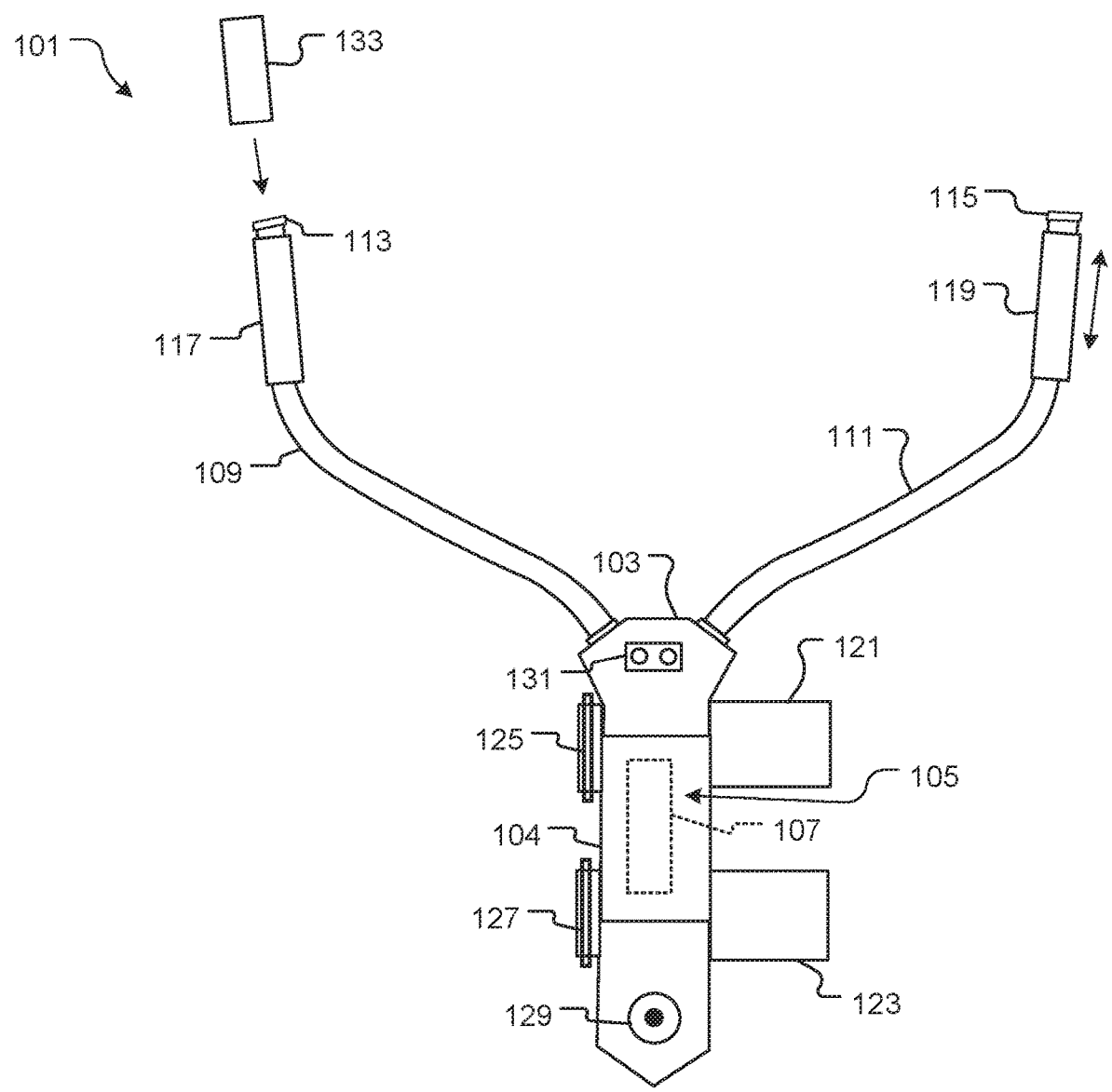
FIG. 1 is a front view of an ophthalmic fixation apparatus in accordance with a preferred embodiment of the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional eye exam systems. Specifically, the present invention provides for an apparatus that includes one or more conduits, a visual indicator of the activation of the targets, and an easy to use toggle switch. These features provide for an improved fixation apparatus for use during eye exams. It should be appreciated that the apparatus of the present invention is specifically configured to be used in connection with slit lamp, either as an individual device, or incorporated permanently into the slit lamp. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a front view of a fixation apparatus 101 in accordance with a preferred embodiment of the present application, the fixation apparatus being portable and usable with any conventional slit lamp. It should be appreciated that in alternative embodiments, the fixation apparatus is permanently incorporated into the slit lamp. It will be appreciated that apparatus 101 overcomes one or more of the above-listed problems commonly associated with conventional eye exam systems.

In the contemplated embodiment, apparatus 101 includes a case housing 103 with a door 104 into an interior area 105 for holding a power source 107. The case housing 103 can vary in size and materials. In the preferred embodiment, the apparatus 101 includes a first conduit 109 and a second conduit 111, the conduits being attached to and extending away from the case housing 103. It should be appreciated that there can be any number of conduits, such as one or more. The conduits 109, 111 house fixation elements 113, 115, such as LED lights, images, objects, shapes, colors, and the like, wherein the fixation elements 113, 115 can be positioned as desired via the flexible conduits, thereby allowing for quick and easy adjustment by the physician or other operator. In some embodiments, the apparatus includes sleeves 117, 119 that can slide and adjust the targeting of the fixation elements. It should be appreciated that the fixation elements provide for improving targeting by the patient's eyes, thereby allowing for an improved examination by the operator. It should also be appreciated that the fixation elements are easily adjusted by having controls easily accessible by the operator during use.

In the preferred embodiment, the housing 103 further includes one or more attachment devices 121, 123 that can include straps, hook and loop style closures, or other similar and suitable closures, such as clasps, buttons, or the like. In addition, the one or more straps can include adjustment devices 125, 127. The one or more straps are configured to provide a means to secure the apparatus 101 to a slit lamp for use. It should further be appreciated that the apparatus 101 can be secured to alternative structures, such as cameras, or the like.

The apparatus 101 can further includes a switch 129 such as a toggle switch, wherein the switch 129 provides for activation and deactivation of the fixation element, such as a light. It should be appreciated that in the preferred embodiment, the physical orientation of the switch correlates to the element. For example, pushing the switch to the left will activate the left light. It should be appreciated that the toggle switch provides for a convenient way for the physician to switch between each side and deactivate the elements as desired. In addition, in some embodiments, the apparatus will include an LED indicator 131, wherein the LED indicator 131 will provide for a visual representation to the user as to which of the sides is activated. Similarly, to the switch, the left indicator light indicates activation of the left side.

It should be appreciated that one of the unique features believed characteristic of the present application is the combination of features, namely the LED indicator, the toggle switch, and the flexible conduits that provide for an easy and efficient fixation targeting for use during eye exams. It should be appreciated that the features can be directly incorporated into a slit lamp, thereby providing for an inclusive apparatus that does not require additional devices being attached thereto. It should be appreciated that the targets can be of any shape and size, and further can be of any color, which will provide for a benefit for patients that may suffer from limited color perception. In addition, in the embodiments wherein the targets are lights, the lights can flash or dim as desired.

It should be appreciated that the use of two conduits allows for easy adjustment by the physician. The apparatus of the present invention can be mounted anywhere on the slit lamp, and therefore provides an almost unlimited bilateral fixation location for the patient and the two conduit arms can be reached much more easily by the eye doctor for either patient eye to see it. In addition, the apparatus allows for two distinct right and left conduit to be used directly above the doctor's right and left hands. The eye doctor need not even look away from the oculars during the exam to locate and manipulate them. The doctor only lifts the right or left hand upward where the conduits emanate from the box housing and move the conduits to wherever the doctor requires without glancing away. If the eye needs a slight alteration in positioning, no words need be spoken as the doctor simply moves the light to that location and the patient follows it as they have already been instructed at the beginning of the exam to "look at the blue/red/white/blinking etc., light".

Figure 2:
FIG. 2 is a top view of a cover of FIG. 1.

The apparatus 101 can further include one or more tubal covers 133, the one or more covers 133 can be configured to provide a color or block out shape for an associated target. This can assist in the exam by changing the target appearance for the patient, as may be desireable. As shown in FIG. 2, a block out shape 201 can be used. Further, the tubal cover 133 can be slid back and forth over the fixation target so that the fixation target can be seen by only one eye at a time. For example, when the tubal cover is pulled distally over the light then the light eminates from a tube and this can be directed to one eye at a time eliminating confusion as to which eye is supposed to see the light. When the tubal cover is pulled back, then both eyes can potentially see the light which can be confusing.

Figure 3:
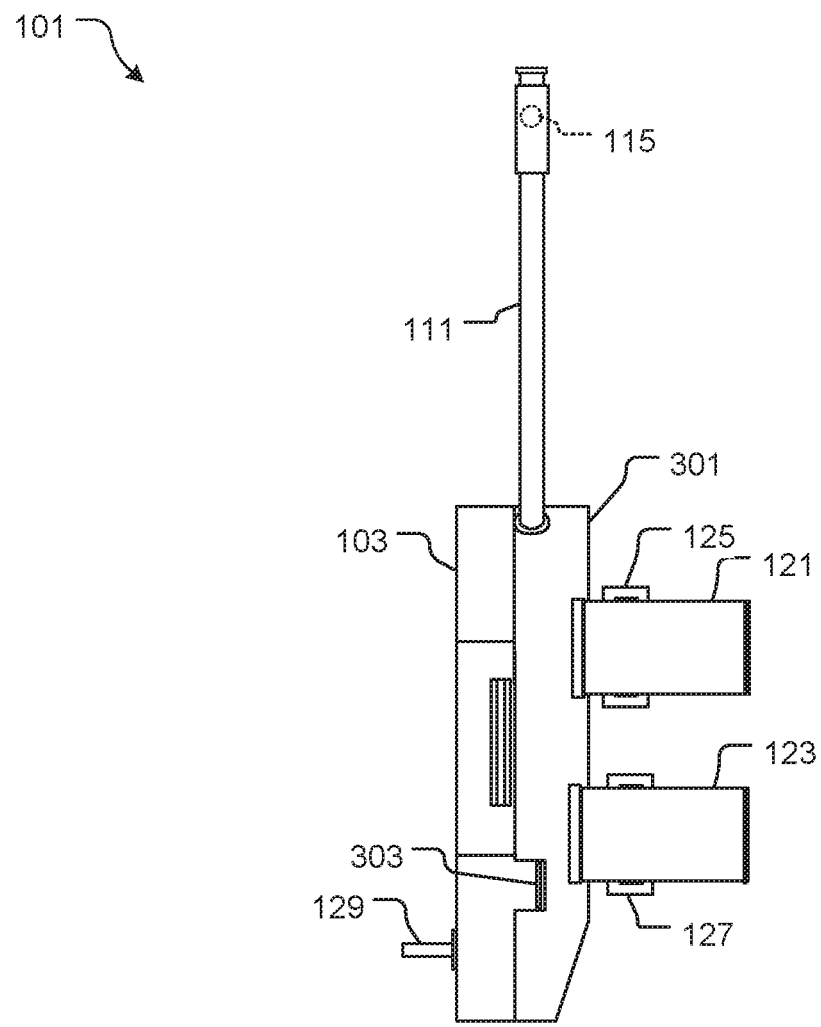
FIG. 3 is a side view of the apparatus of FIG. 1.

In FIG. 3, a side view further depicts apparatus 101. As shown, in some embodiments, a foam pad 301 can be secured to the case housing 103, thereby allowing for adjustability in securing to various models and styles of slit lamps. In addition, a brightness adjustor 303 such as a wheel can be provided to allow for adjustment of the fixation elements, such as lights.

Figure 4:
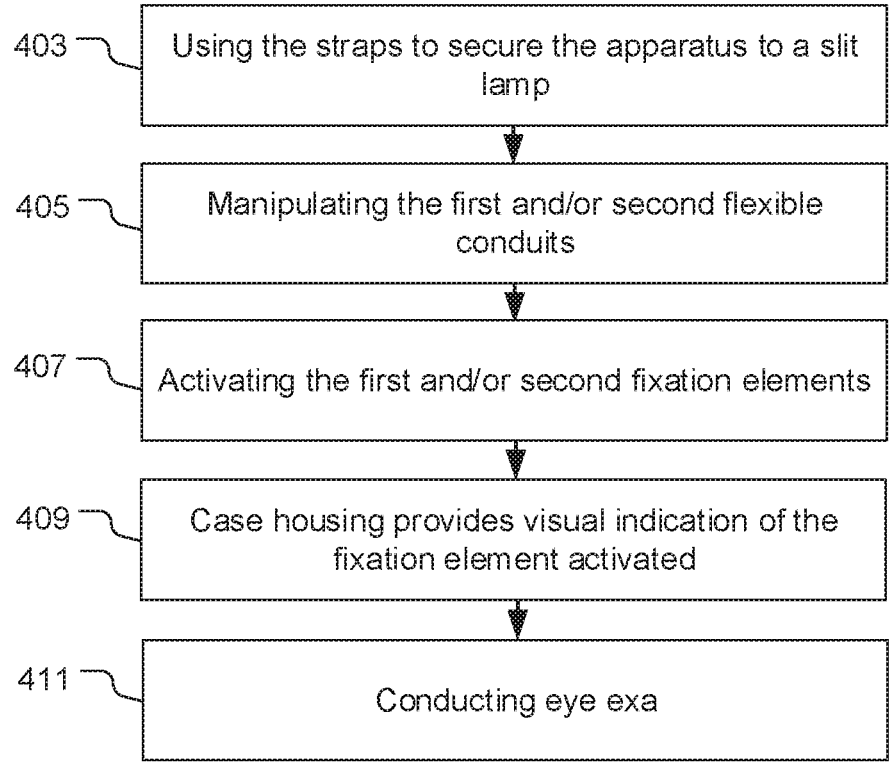
FIG. 4 is a flowchart of a method of use of the apparatus of FIG. 1.

In FIG. 4, a flowchart 401 depicts the method of use of the apparatus 101. During use, the apparatus is secured to a slit lamp via the one or more attachment devices and the one or more fixation elements are adjusted via manipulation of the first and second conduits, as shown with boxes 403, 405. The user can then activate the fixation elements, such as lights, and adjust brightness as needed, wherein the case housing provides a visual indication of the side activated, as shown with boxes 407, 409. The operator can then conduct an eye exam, as shown with box 411. It should be further appreciated that as needed and desired, the operator can remove the apparatus and secure it to another device, or reposition the apparatus as needed.

An alternative embodiment could utilize Bluetooth technology or other sensors inside the housing or affixed to the bottom outside of the slit lamp that is attuned to the location of the slit lamp via a metal strip mounted below the slit lamp on the table. When the slit lamp is moved to the right eye or left eye the sensor would necessarily cross over the metal strip on the slit lamp table below activating the sensor and relaying a signal to the conduit lights telling which light to turn on. When the slit lamp is moved to evaluate the right eye, it will move to the right which would automatically turn on the Left conduit light for left eye fixation which makes the right eye still for examination. Vice versa when the slit lamp moves to the left eye.

It should be appreciated that the features of the apparatus explained herein can all be physically incorporated into any future slit lamps that are newly produced with a right and left toggle switch incorporated into the joystick itself (or anywhere in the total slit lamp/table/head rest complex) and right and left fixation lights either on conduits or mounted to the eye doctor side of the slit lamp (or anywhere else not traditionally produced on manufactured on slit lamp apparatuses) facing the patient.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An ophthalmic fixation apparatus, comprising:
   a case housing with an interior area configured to hold a power source, the case housing further having a switch configured to activate one or more fixation elements;
   one or more attachment devices extending from the case housing, the one or more attachment devices to secure the apparatus to a slit lamp; and
   one or more flexible conduits extending from the case housing and configured to facilitate direction of the one or more fixation elements;
   wherein the ophthalmic fixation apparatus is configured for use during an eye exam to improve patient fixation for ease of examination and improved efficiency.

2. The apparatus of claim 1, wherein the one or more attachment devices include hook and loop fasteners.

3. The apparatus of claim 1, wherein the case housing further comprises a removable cover to provide access to the power source.

4. The apparatus of claim 1, wherein the switch is a toggle switch.

5. The apparatus of claim 1, further comprising:
   a cover configured to secure over an end of the first conduit.

6. The apparatus of claim 5, wherein the cover includes a shape for a patient to focus on during examination.

7. The apparatus of claim 5, wherein the cover includes a color.

8. The apparatus of claim 5, wherein the cover acts as a sleeve to slide over the first conduit to provide increased directionality of one of the one or more fixation elements.

9. The apparatus of claim 1, wherein the case housing further includes:
   an LED indicator that is configured to indicate which of the one or more fixation elements is activated.

10. The apparatus of claim 1, wherein the one or more fixation elements are one or more lights.

11. The apparatus of claim 10, wherein the one or more lights are configured to be activated to blink and can further include a brightness adjustment.

12. The apparatus of claim 11, further comprising:
    a brightness dial extending from the case housing and configured to alter a brightness level of the one or more lights.

13. The apparatus of claim 1, further comprising:
    a foam pad secured to a back of the case housing, the foam pad allowing for securing to the slit lamp regardless of a shape associated with the slit lamp.

14. The apparatus of claim 1, wherein the attachment device is one or more straps.

15. A method of eye exam, the method comprising:
    providing the ophthalmic fixation apparatus of claim 1;
    securing the ophthalmic fixation apparatus to a slit lamp;
    activating one of the one or more fixation elements; and
    conducting an eye exam.

16. The method of claim 15, further comprising:
    moving the ophthalmic fixation apparatus to a second structure.

17. The method of claim 15, further comprising:
    adjusting the ophthalmic fixation apparatus to a different location on the slit lamp such that the ophthalmic fixation apparatus is easily adjusted by an operator to improve efficiency.

18. The method of claim 15, further comprising:
    sliding a cover over one of the one or more fixation elements to increase directionality of the one of the one or more fixation elements.

* * * * *